United States Patent
Sendai

(10) Patent No.: US 7,778,388 B2
(45) Date of Patent: Aug. 17, 2010

(54) RADIATION TOMOGRAPHIC IMAGE GENERATION APPARATUS

(75) Inventor: Tomonari Sendai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 274 days.

(21) Appl. No.: 11/928,724

(22) Filed: Oct. 30, 2007

(65) Prior Publication Data

US 2008/0101536 A1   May 1, 2008

(30) Foreign Application Priority Data

Oct. 31, 2006  (JP) ............................ 2006-295400

(51) Int. Cl.
*A61B 6/00* (2006.01)
(52) U.S. Cl. ......................................... 378/22; 378/37
(58) Field of Classification Search ............... 378/22, 378/37
See application file for complete search history.

(56) References Cited

U.S. PATENT DOCUMENTS

| | | | | |
|---|---|---|---|---|
| 4,903,204 A * | 2/1990 | Dobbins, III | ................ | 382/255 |
| 6,611,575 B1 | 8/2003 | Alyassin et al. | | |
| 2001/0038681 A1 * | 11/2001 | Stanton et al. | ................ | 378/55 |
| 2003/0076920 A1 * | 4/2003 | Shinno et al. | ................... | 378/4 |
| 2003/0194050 A1 | 10/2003 | Eberhard et al. | | |
| 2005/0105678 A1 * | 5/2005 | Nakashima | ..................... | 378/4 |
| 2007/0036265 A1 * | 2/2007 | Jing et al. | ...................... | 378/37 |
| 2007/0242797 A1 * | 10/2007 | Stewart et al. | ................ | 378/16 |

OTHER PUBLICATIONS

Wu et al., Tomographic mammography using a limited number of low-dose cone-beam projection images, Med Phys, 30, Mar. 3, 2003, pp. 365-380.*
Jun Wei et al., Convergence Index Filter for Detection of Lung Nodule Candidates, Transactions of The Institute of Electronics, Information and Communication Engineers, 2000, pp. 118-125, vol. J83-D-II, No. 1.

* cited by examiner

*Primary Examiner*—Edward J Glick
*Assistant Examiner*—Alexander H Taningco
(74) *Attorney, Agent, or Firm*—Sughrue Mion, PLLC

(57) ABSTRACT

A tomographic image generation apparatus for generating tomographic images appropriate for diagnosis from radiation images obtained by tomosynthesis imaging. Tomographic images of a subject are generated with a first slice interval by reconstructing a plurality of radiation images obtained by the tomosynthesis imaging. A region of interest is detected from the tomographic images generated with the first slice interval. Tomographic images are generated with a second slice interval, which is smaller than the first slice interval, adjacent to the slice position of a tomographic image from which a region of interest is detected.

7 Claims, 16 Drawing Sheets

FIG.11
| $f_{11}$ | $f_{12}$ | $f_{13}$ | $f_{14}$ | $f_{15}$ |
|---|---|---|---|---|
| $f_{21}$ | | | | $f_{25}$ |
| $f_{31}$ | | $j$ | | $f_{35}$ |
| $f_{41}$ | | | | $f_{45}$ |
| $f_{51}$ | $f_{52}$ | $f_{53}$ | $f_{54}$ | $f_{55}$ |
FIG.12
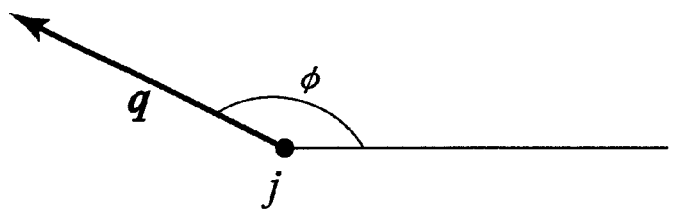
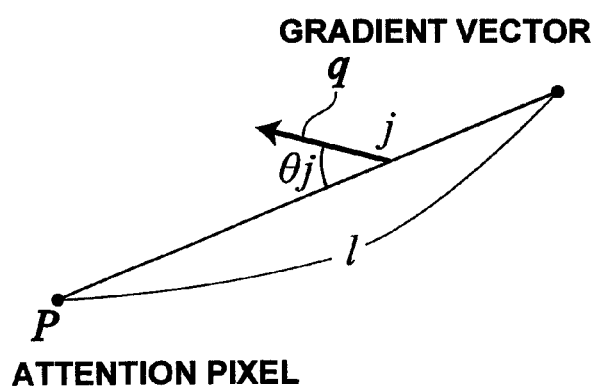
GRADIENT VECTOR
$q$
ATTENTION PIXEL

ATTENTION PIXEL

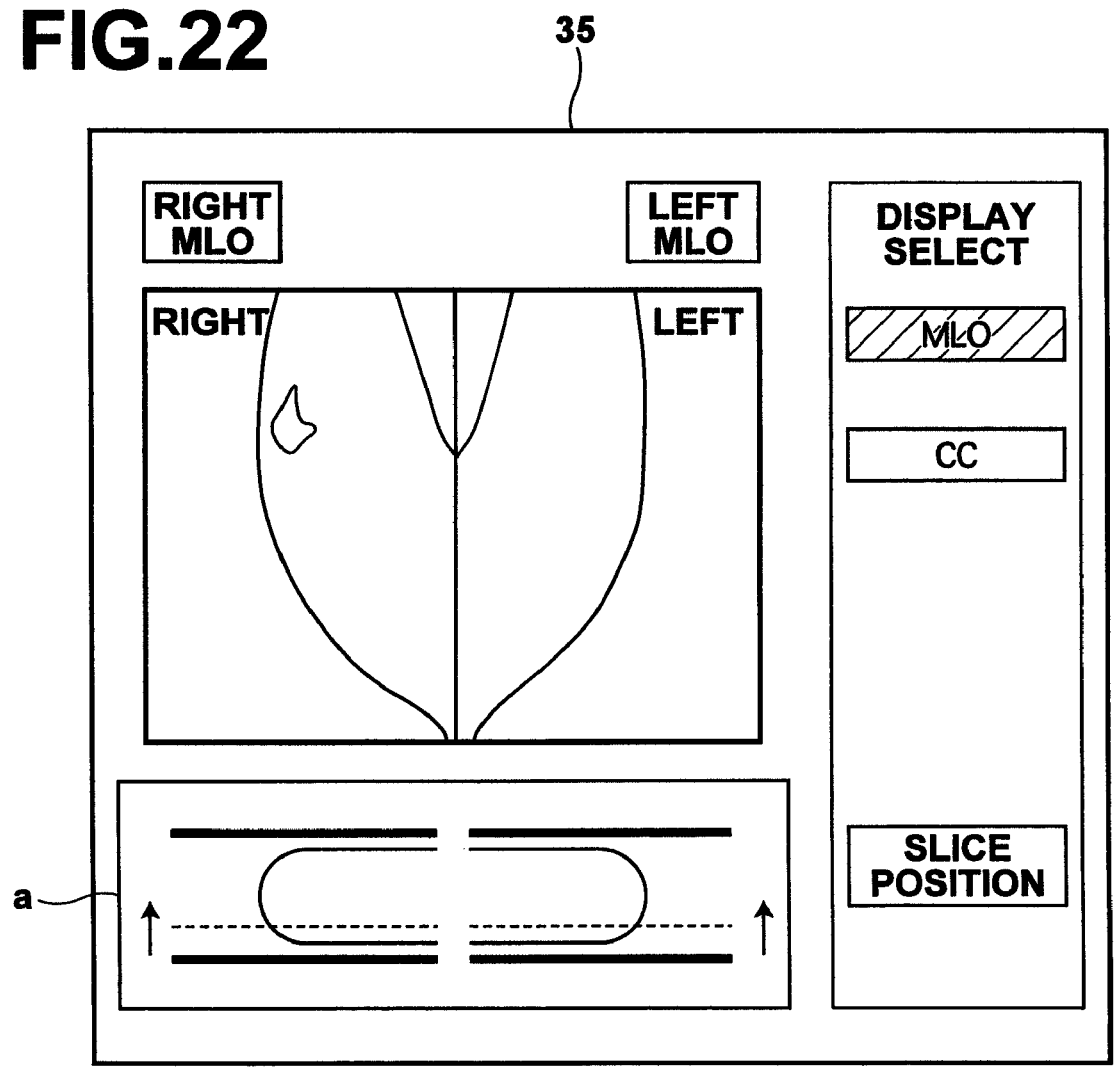

US 7,778,388 B2

RADIATION TOMOGRAPHIC IMAGE GENERATION APPARATUS

BACKGROUND OF THE INVENTION

1. Field of the Invention

The present invention relates to a radiation tomographic image obtaining apparatus for obtaining tomographic images through radiation imaging.

2. Description of the Related Art

Mammography based on plain X-ray imaging is performed for breast cancer screening. Sensitivity of the mammography, however, is relatively low and the screening result is highly likely to be false positive. Consequently, diagnosis is performed by the plain X-ray imaging in the screening first, and if the screening result shows a possibility of breast cancer, another diagnosis using another modality (CT, MRI, or the like) is performed. Different modalities have different applications. For example, the mammography through plain X-ray imaging is used for detecting small calcifications and tumors. CT and MRI may obtain more amount of information and determine whether a detected tumor is benign or malignant. In mammography, a breast is squeezed while it is imaged. On the other hand, CT or MRI requires no breast compression. Thus, it is difficult to identify the corresponding positions between the mammography image and CT or MRI image, and therefore these images are unable to be used effectively in the diagnosis.

Consequently, researches have been conducted for a method of obtaining a breast tomographic image by tomosynthesis in which a plurality of radiation images are obtained by compressing a breast placed on a detector with a pressing plate and arcing an X-ray source with respect to the breast and detector, and a tomographic image is reconstructed on a plane parallel to the detection surface of the detector by translating the plurality of radiation images and adding the images after adjusting the sizes thereof.

The use of the tomosynthesis technique allows tomographic images sliced at an interval of, for example, 1.0 mm to be reconstructed. Further, boxel data including data samples $N_x \times N_y \times N_z$ along X, Y, and Z axes respectively may be generated by reconstructing a plurality of tomographic images in the manner as described above. A method and system for generating a 3D image using the boxel data is proposed as described, for example, in U.S. Pat. No. 6,611,575.

Further, a system in which a 3D image is generated using an image reconstruction algorithm and visualized using a volume rendering mode or a cinema (motion image) mode is proposed as described, for example, in U.S. Patent Application Publication No. 20030194050.

A demand exists that, when performing a diagnostic observation, a detailed observation be allowed for a region of affected area, as well as all of the tomographic images obtained. Further, it is effective to make a comparison with an image obtained in the past, or, for pair organs like breasts, it is effective to make comparison between the right and left organs.

In view of the circumstances described above, it is an object of the present invention to provide a radiation tomographic image generation apparatus for generating tomographic images appropriate for diagnosis from radiation images obtained by tomosynthesis imaging. It is a further object of the present invention to provide a computer readable recording medium on which a program for causing a computer to perform functions of the apparatus.

SUMMARY OF THE INVENTION

The radiation tomographic image generation apparatus of the present invention is an apparatus including:

a radiation image storage means for storing a plurality of radiation images obtained from a radiation image detector by irradiating radiation to a subject on the radiation image detector from different directions by moving a radiation irradiation section, which is provided opposite to the radiation image detector, to a plurality of positions and irradiating the radiation from the radiation irradiation section in each of the positions;

a tomographic image reconstruction means for reconstructing the plurality of images stored in the radiation image storage means to generate a tomographic image of the subject which is parallel to the detection surface of the radiation image detector;

a first tomographic image generation means for generating a plurality of tomographic images with a first slice interval using the tomographic image reconstruction means;

a region of interest detection means for detecting a region of interest from the tomographic images generated with the first slice interval; and a second tomographic image generation means for generating tomographic images with a second slice interval, which is smaller than the first slice interval, adjacent to the slice position of a tomographic image from which a region of interest is detected by the region of interest detection means using the tomographic image reconstruction means.

The computer readable recording medium of the present invention is a medium on which a program for causing a computer to perform the following functions:

a tomographic image reconstruction means for reconstructing a plurality of radiation images stored in a radiation image storage means storing a plurality of radiation images obtained from a radiation image detector by irradiating radiation to a subject on the radiation image detector from different directions by moving a radiation irradiation section, which is provided opposite to the radiation image detector, to a plurality of positions and irradiating the radiation from the radiation irradiation section in each of the positions to generate a tomographic image of the subject which is parallel to the detection surface of the radiation image detector;

a first tomographic image generation means for generating a plurality of tomographic images with a first slice interval using the tomographic image reconstruction means;

a region of interest detection means for detecting a region of interest from the tomographic images generated with the first slice interval; and a second tomographic image generation means for generating tomographic images with a second slice interval, which is smaller than the first slice interval, adjacent to the slice position of a tomographic image from which a region of interest is detected by the region of interest detection means using the tomographic image reconstruction means.

The referent of "region of interest" as used herein means a region which is desirable to be carefully observed, such as a region where a tumor pattern or the like is imaged.

The radiation tomographic image generation apparatus of the present invention may further includes a high dose image storage means for storing a high dose image obtained by irradiating higher dose radiation to the subject than the radiation for obtaining the plurality of radiation images used for the reconstruction of tomographic image, and the region of interest detection means may be a means for detecting a region of interest from the high dose image and, in consideration of the position of the detected region of interest, detecting a region of interest from each of the tomographic images.

Further, the apparatus may further includes a tomographic image display means for sequentially displaying the tomographic images in the order of the depth thereof, and the tomographic image display means may be a means for performing the display such that the change in the depth of displaying tomographic images becomes temporally constant by making the time interval for displaying the tomographic images generated with the second slice interval shorter than the time interval for displaying the tomographic images generated with the first slice interval.

The referent of "depth" as used herein means a distance from the radiation image detector, and the referent of "sequentially displaying the tomographic images in the order of the depth thereof" as used herein means that the tomographic images are switched and displayed from a tomographic image adjacent to the radiation image detector toward a radiation image remote from the detector, or from the tomographic image remote from the detector toward the tomographic image adjacent to the detector.

The tomographic image display means may be a means for displaying two sets of tomographic images, generated respectively from two sets of radiation images of the same region or symmetrical regions of the subject, side by side on the screen by switching the tomographic images in the order of the depth thereof, and such that the tomographic images of the same depth, each in each of the sets of tomographic images, are displayed at the same time.

The referent of "symmetrical regions" as used herein means structurally symmetrical organs or tissues, such as right and left breasts.

According to the present invention, when tomographic images are generated by reconstructing radiation images obtained through tomosynthesis imaging, tomographic images are additionally generated with a smaller slice interval before and after a tomographic image from which a region of interest showing a tumor-like pattern is detected. This allows the observer to correctly determine whether or not the detected pattern is a tumor. In this way, tomographic images are generated for the region of interest, so that the size, shape, and the like of the tumor may be recognized.

Further, by detecting a region of interest from a radiation image obtained by irradiating high dose radiation used in plain X-ray imaging and, with reference to the position of the detected region of interest, detecting a region of interest from tomographic images reconstructed from the radiation images obtained through the tomosynthesis imaging, the region of interest appearing on the radiation image obtained through the plain X-ray imaging may be closely observed.

Still further, by sequentially displaying the tomographic images in the order of the depth thereof, and such that the change in the depth of the displayed tomographic images becomes temporally constant, the change in the images in the depth direction may be observed at a constant speed even in the region including tomographic images generated with a smaller slice interval, which facilitates the recognition of the size and position of a tumor or the like.

Further, by displaying two sets of tomographic images generated respectively from two sets of comparable radiation images, such as past and current images of the same region, or right and left breasts, such that the tomographic images of the same depth, each in each of the sets of tomographic images, are displayed at the same time. This facilitates image comparison and correct diagnosis.

BRIEF DESCRIPTION OF THE DRAWINGS

FIG. 11 illustrates a density gradient.

FIG. 12 illustrates the relationship between a gradient vector and an attention pixel (part 1).

FIG. 22 illustrates an example display in which an indicator indicating the slice position of a tomographic image is provided.

DESCRIPTION OF THE PREFERRED EMBODIMENTS

Hereinafter, the radiation tomographic image obtaining apparatus according to a first embodiment will be described in detail with reference to the accompanying drawings. In the present embodiment, a radiation tomographic image obtaining apparatus, which includes a breast image obtaining unit that combines mammography and tomosynthesis functions and performs tomosynthesis imaging for a breast placed on the imaging platform while the breast is being compressed with the pressing plate, will be described.

Figure 1:
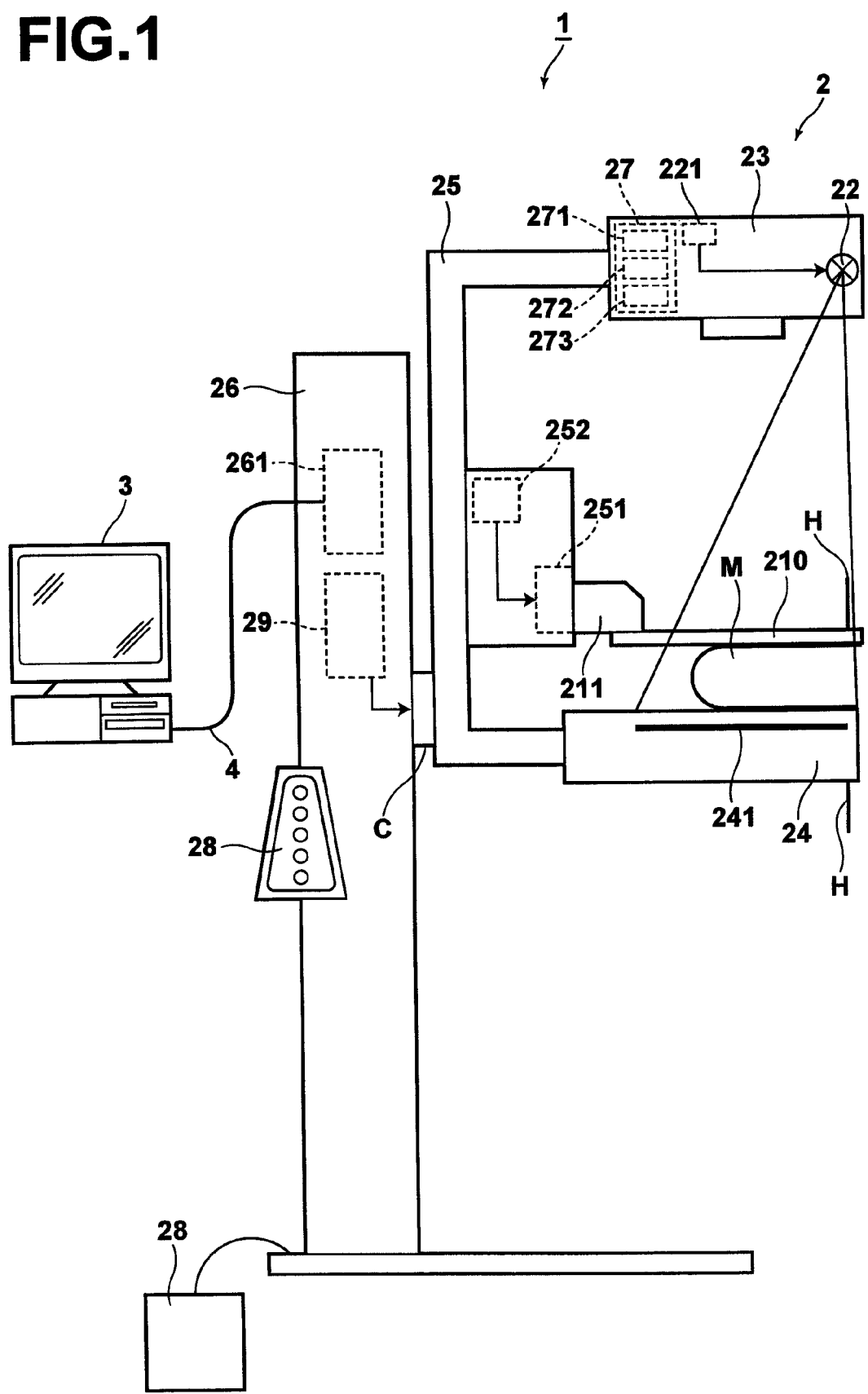
FIG. 1 is a block diagram of the radiation tomographic image obtaining apparatus according to a first embodiment of the present invention.
Figure 2:
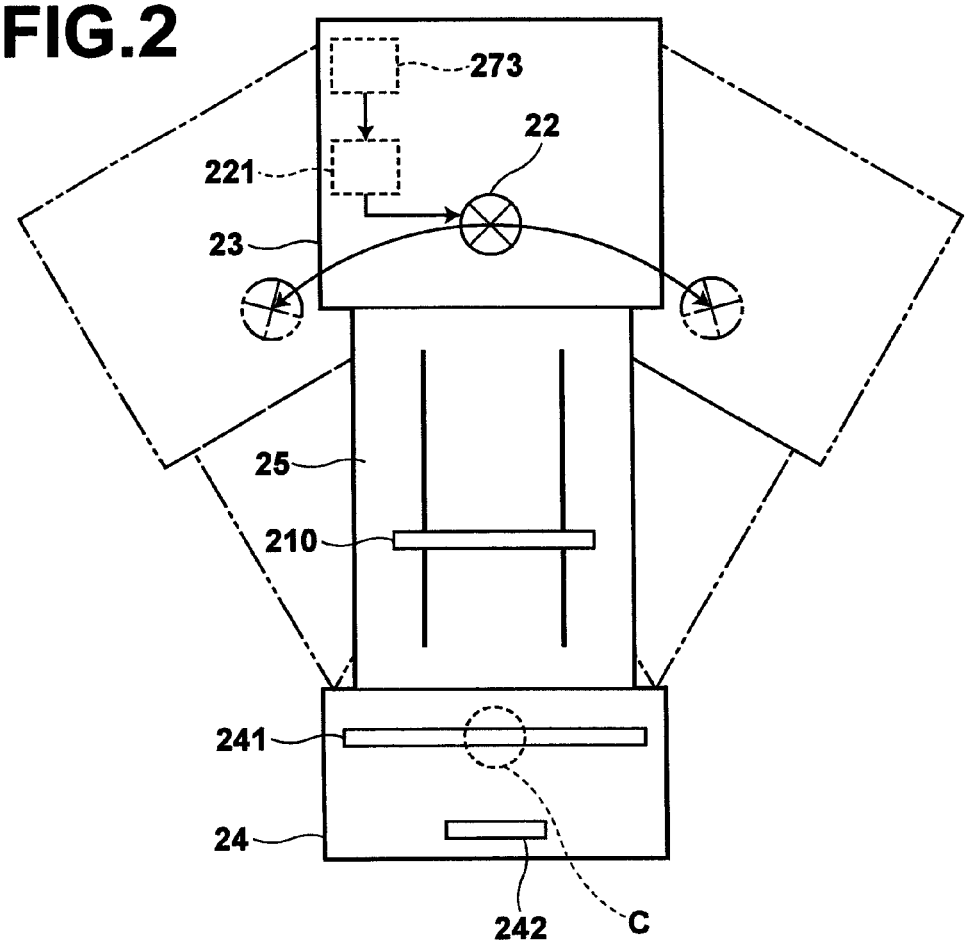
FIG. 2 is a front view of an arm section of a breast image obtaining unit.

FIG. 1 is a schematic block diagram of a radiation tomographic image obtaining apparatus of the present invention. FIG. 2 is a front view of an arm section of the breast image obtaining unit constituting the radiation tomographic image obtaining apparatus.

The radiation tomographic image obtaining apparatus 1 includes: a breast image obtaining unit 2 for obtaining a plurality of radiation images of a breast of a subject by irradiating radiation to the breast from different directions; a tomographic image generation unit 3 for generating a tomographic image by reconstructing the plurality of radiation images obtained by the breast image obtaining unit 2; and a network 4 linking the breast image obtaining unit 2 and the tomographic image generation unit 3.

The breast image obtaining unit apparatus 2 includes: an arm 5 connecting a radiation accommodation section 23 accommodating therein a radiation irradiation section (radiation source) 22 and imaging platform 24 having therein a recording medium holding section, such as a cassette or the like, in which a radiation image detector 241, such as a flat panel detector or the like, is accommodated such that they face each other; a base 26 for connecting the arm 25 through a spindle C; a control section 27 for controlling the radiation accommodation section 23; and a transmission section 261 for sending data including obtained radiation image data to the tomographic image generation unit 3 through the network 4.

The base 26 further includes: an operation section 28 for use by the operator to control the height, amount and direction of rotation of the arm 25; and an arm moving means 29 for vertically and rotationally moving the arm 25 according to the input from the operation section 28.

Between the radiation accommodation section 23 and imaging platform 24, the arm 25 includes: a mounting section 251 for mounting a pressing plate 210 that compresses a breast M by pressing it onto the imaging platform 24 from above; a pressing plate moving means 252 for moving the mounting section 251 along the vertical directions of the arm 25.

The pressing plate 210 includes an insertion section 211, which is inserted into the mounting section 251 of the arm 25.

Figure 3:
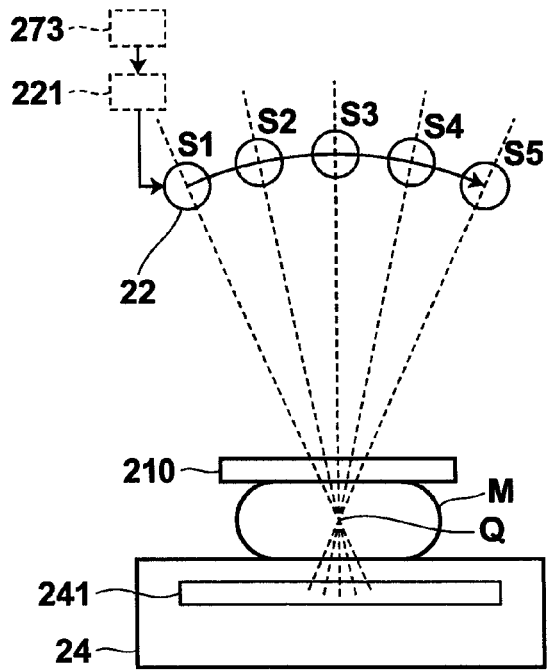
FIG. 3 illustrates movement of the radiation source.

The radiation accommodation section 23 includes therein the radiation source 22, and also includes a radiation source moving means 221 (FIG. 3) for moving the radiation source 22 in arc in the direction along the sides of the imaging platform 24 toward the chest wall of a subject (normally, the long sides of the rectangular imaging platform 24) by rotating the radiation accommodation section 23 around the spindle C.

The radiation source 22 irradiates radiation toward the breast M placed on the imaging platform 24 at different imaging angles from each of positions S1, S2, - - -, SN while moving in arc. When the breast M is imaged, the breast M is placed on the imaging platform 24 and pressed by the pressing plate 210 from above, so the thickness of the breast M becomes approximately 4 to 5 cm. Therefore, it is preferable that the radiation be irradiated by the radiation source 22 in each of the positions toward a point Q (irradiation point) which is approximately 2 cm above the center of the imaging surface of the imaging platform 24 (more specifically, a position which becomes the center of the breast M when placed on the surface of the imaging platform 24) in order to obtain an appropriate image for the observation of the breast M.

Arranged inside of the imaging platform 24 are a flat detector 241 that receives radiation irradiated from the radiation source to record image information according to the dose of radiation transmitted through the breast M, and outputs image data representing the recorded image information, and a dose detector 242 for detecting the dose of radiation irradiated from the radiation accommodation section 23 and transmitted through the breast M, which is disposed under the flat panel detector 241, as illustrate in FIG. 2.

The spindle C, which is the center of rotation, is attached to the base 26 at the position corresponding to the center of the flat panel detector 241 so that the rotation center of the arm 25 corresponds to the center of the flat panel detector 241, and the arm 25 is attached to the base 26 through the spindle C (FIG. 2).

Hereinafter, the structure of the imaging platform 24 when the radiation image detector 241 is a flat panel detector will be described with reference to FIGS. 4 to 7.

Figure 4:
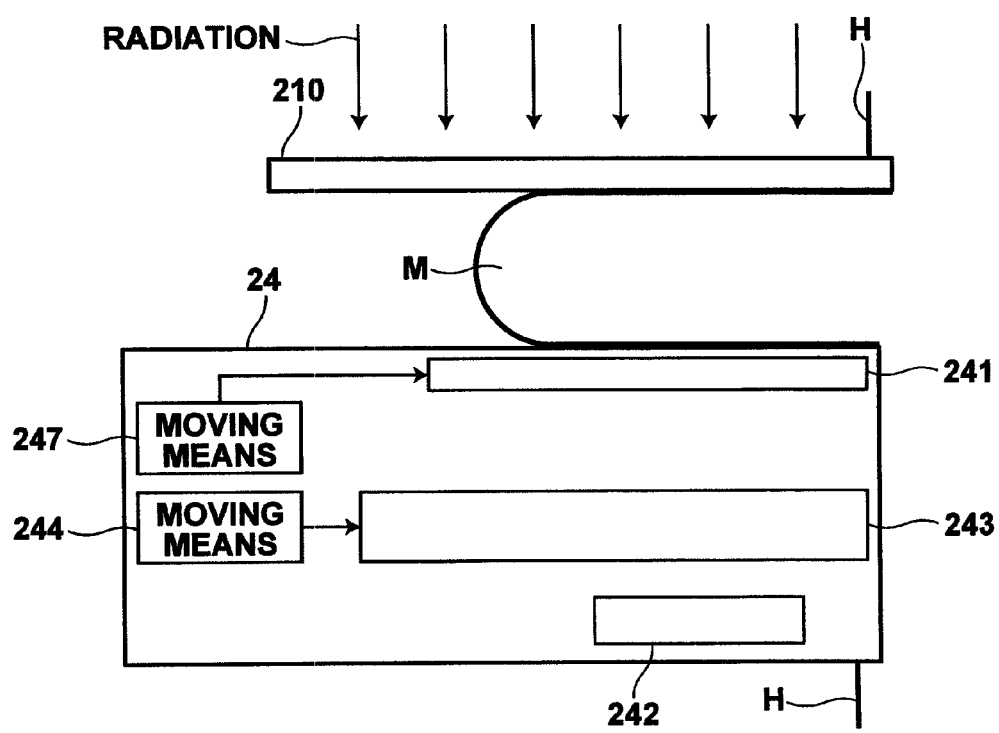
FIG. 4 illustrates the relationship among a pressing plate, and a solid state detector and a dose detector within an imaging platform.

As illustrated in FIG. 4, arranged inside of the imaging platform 24 are: a readout exposure light source section 243 used when reading out image information recorded on the radiation image detector 241; a readout exposure light source section moving means 244 for moving the readout exposure light source section 243 in the sub-scanning directions; a current detection means 245 for detecting currents flowing out from the radiation image detector 241 when scan exposed by the readout exposure light source section 243 to obtain image signals; a high voltage power source section 246 for applying a predetermined voltage to the radiation image detector 241; a pre-exposure light source section 260 for irradiating pre-exposure light on the radiation image detector 241 prior to initiating imaging; a radiation image detector moving means 247 for moving the radiation image detector 241 in the directions toward and away from the chest wall H of the subject (sub-scanning directions described above) within the imaging platform 24; and a control means 248 for controlling the readout exposure light source section 243, current detection means 245, high voltage power source section 246, pre-exposure light source section 260, and moving means 247 and 244.

Figure 6:
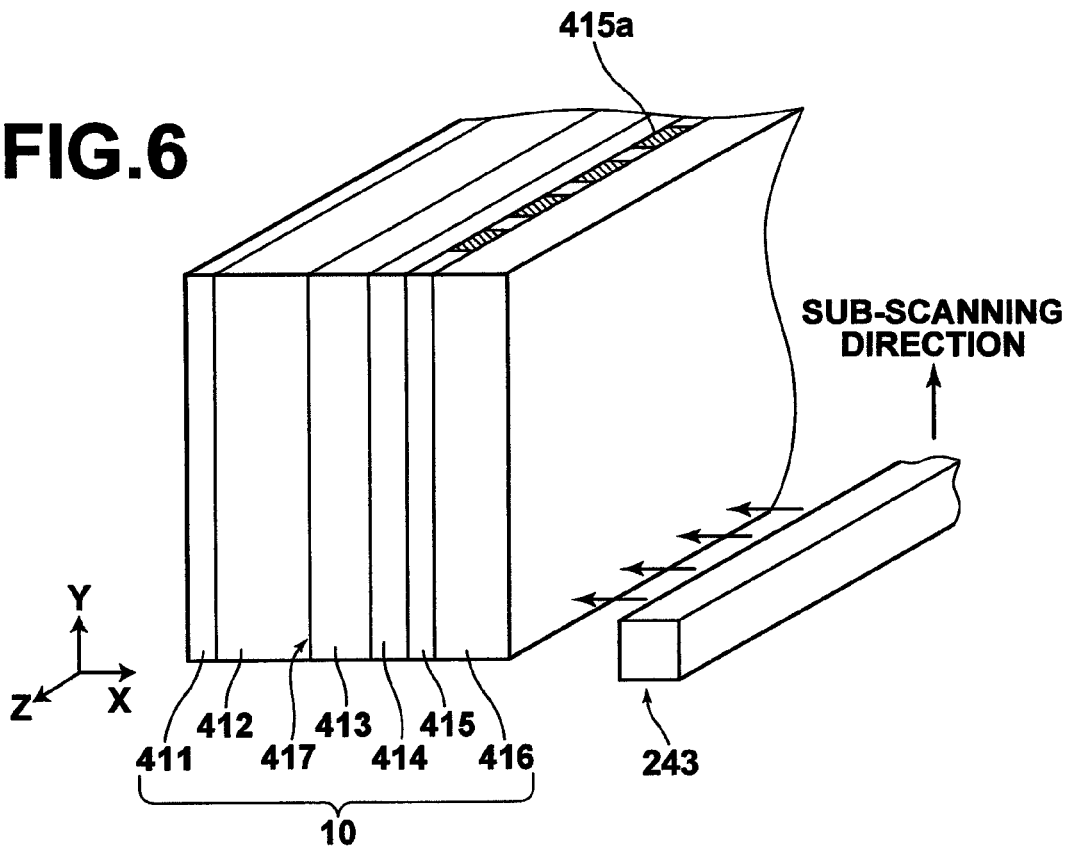
FIG. 6 illustrates an overview of a radiation image detector (solid state detector).

The radiation image detector 241 is a direct conversion/optical readout type solid state radiation detector, which receives recording light representing image information to record the image information as an electrostatic latent image, and is scanned by readout light to generate currents according to the electrostatic latent image. More specifically, as shown in FIG. 6, it includes a glass substrate on which the following layers are stacked in the order listed below: a first conductive layer 411 which is transparent to the radiation (recording light) transmitted through the breast M; a recording photoconductive layer 412 that generates charges and shows electrical conductivity by receiving the recording light; a charge transport layer 413 that acts substantially as an insulator against charges having the polarity of latent image charges charged on the first conductive layer 411, and substantially as a conductor for transport charges having the opposite polarity to that of the latent image charges; a readout photoconductive layer 414 that generates charges and shows electrical conductivity by receiving readout light; and a second conductive layer 415 which is transparent to the readout light. In addition, a storage section 417 is formed at the interface between the recording photoconductive layer 412 and charge transport layer 413.

The first conductive layer 411 and second conductive layer 415 are electrode layers. The electrode of the first conductive layer 411 is a plate electrode which is two dimensionally flat, and the electrode of the second conductive layer 415 is a striped electrode constituted by multitudes of elements (line electrodes) 415a for detecting the recorded information as image signals arranged in stripes at a pixel pitch as shown in hatched lines in FIG. 6 (refer for example, to the electrostatic recording medium described in Japanese Unexamined Patent Publication No. 2000-105297 for detail). The arrangement direction of the elements 415a corresponds to the main scanning directions, and the longitudinal direction of the elements 415a corresponds to the sub-scanning directions.

The solid state detector 241 has a long side of 30 cm and a short side of 24 cm so as to be able to accept a large breast, and is arranged in the imaging platform 24 such that the long side directions correspond to the main scanning directions and the short side directions correspond to the sub-scanning directions.

As for the readout exposure light source section 243, a light source constituted by a line light source having a plurality of LED chips arranged in a line, and an optical system for irradiating the light outputted from the line light source on the solid state detector 241 in a line. The entire surface of the solid state detector 241 is exposed by scanning the light source section 243 in the longitudinal direction of the striped electrodes 415a of the detector 241, i.e., the sub-scanning directions by the moving means 244 constituted by a linear motor with a required distance between the light source section 243 and solid state detector 241 maintained. The readout exposure light source section 243 and the moving means 244 constitute the readout light scanning means.

Figure 7:
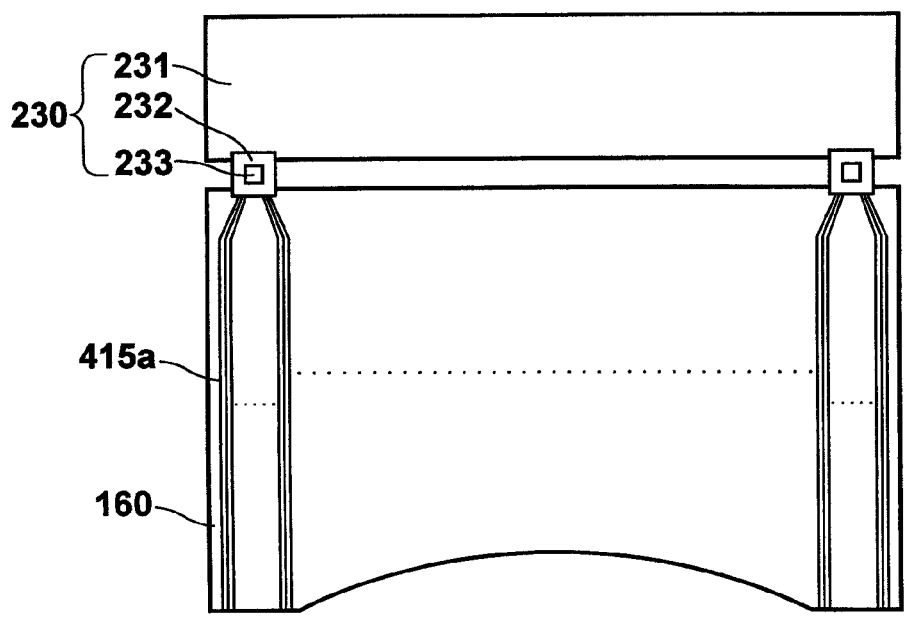
FIG. 7 illustrates a connection aspect of a current detection means to the radiation image detector.

FIG. 7 illustrates in detail a connection aspect of the current detection means 245 to the sold state detector 241. As illustrated, each element 415a is connected to a charge amplifier IC 233 through a printed pattern (not shown) formed on a TAB (tape automated bonding) film on the side of the detector 241 to be contacted with the chest wall H of a subject. Further, the charge amplifier IC 233 is connected to a printed circuit board 231 through a printed pattern (not shown) formed on the TAB film 232. In the present embodiment, instead of connecting all of the elements 415a to a single charge amplifier IC 233, several to several tens of charge amplifier ICs are provided, and every several to several hundreds of elements 415a are connected to each charge amplifier IC 233.

The embodiment of the current detection means 245 is not limited to that described above, and it may be embodied as so-called COG (chip on glass) in which the charge amplifier ICs 233 are formed on the glass substrate 416 instead of the TAB film.

Figure 8:
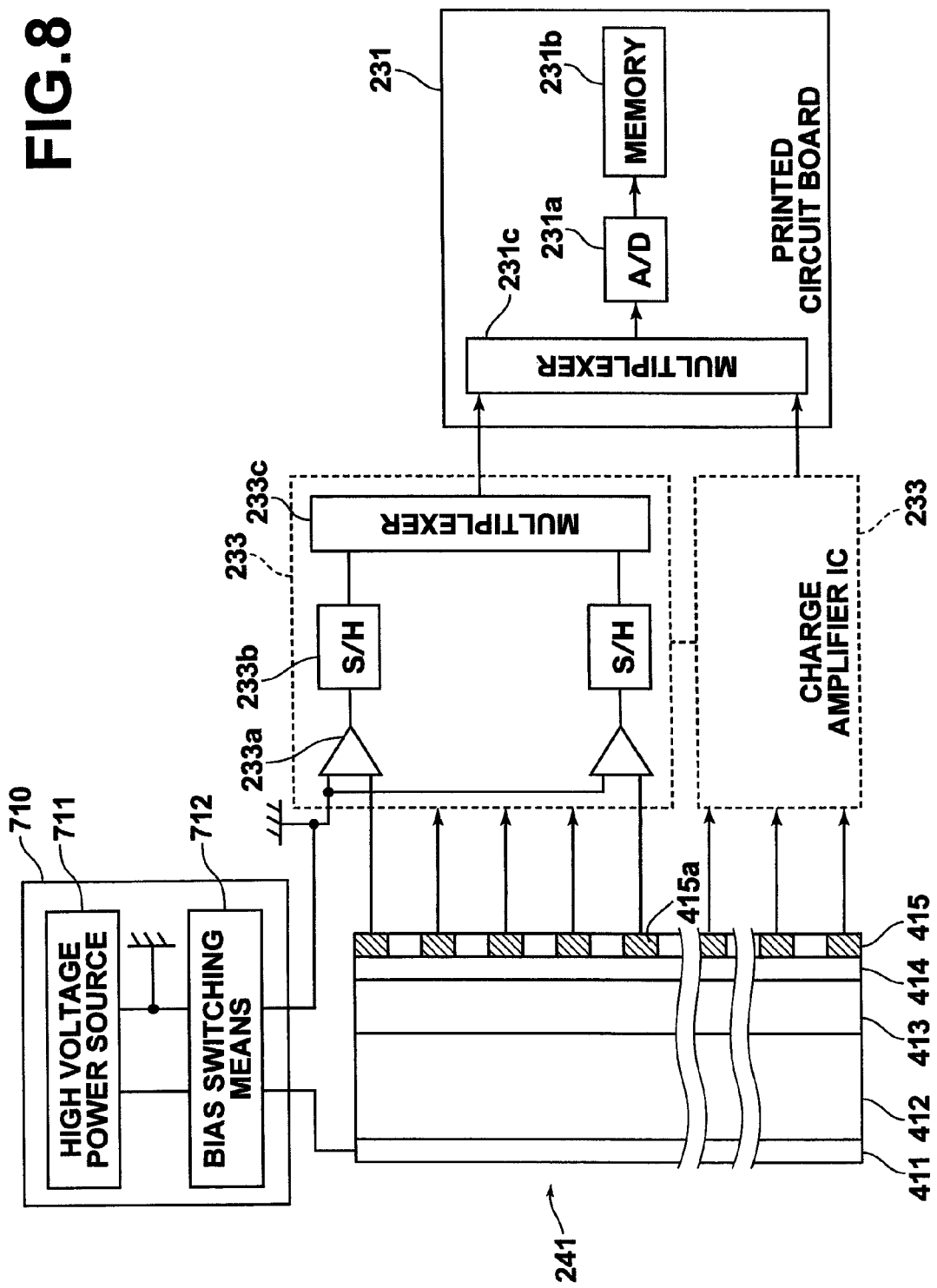
FIG. 8 is a block diagram illustrating the detail of the current detection means and high voltage power source, and a connection aspect of the detection means and high voltage power source to the solid state detector.

FIG. 8 is a block diagram illustrating the detail of the current detection means 245 and high voltage power source section 710 provided in the imaging platform 24, and the connection aspect thereof to the solid state detector 241.

The high voltage power source section 710 is a circuit in which a high voltage power source 711 and a bias switching means 712 are integrated. The high voltage power source 711 is connected to the electrostatic recording section 241 through the bias switching means 712 that performs switching for applying a bias voltage to the electrostatic recording section 241, or shunting the recording section 241 to ground. The circuit is a charge/discharge surge current suppression design, in which a peak current that flows at the time of switching is limited to prevent any destruction of the sections of the apparatus where the currents are concentrated.

The charge amplifier IC 233 formed on the TAB film includes: multitudes of charge amplifiers 233a, each connected to each element 415a of the solid state detector 241; a sample-and-hold (S/H) circuit 233b connected to each charge amplifier 233a; and a multiplexer 233c for multiplexing the signal outputted from each S/H circuit. The current flowing out of the solid state detector 241 is converted by each charge amplifier 233a to a voltage, which is sampled and held by the S/H circuit 233b at a predetermined timing. The voltage sampled and held by each S/H circuit, which corresponds to each element 415a, is sequentially outputted from the multiplexer 233c so as to be switched in the arrangement order of the elements 415a (corresponding to a part of the main scanning). The signals sequentially outputted from the multiplexer 233c are inputted to a multiplexer 231c provided on the printed circuit board 231, and the voltage corresponding to each element 415a is sequentially outputted from the multiplexer 231c so as to be switched in the arrangement order of the elements 415a, thereby the main scanning is completed. The signals sequentially outputted from the multiplexer 231c are converted to digital signals by an A/D converter 231a, and stored in a memory 231b.

Figure 5:
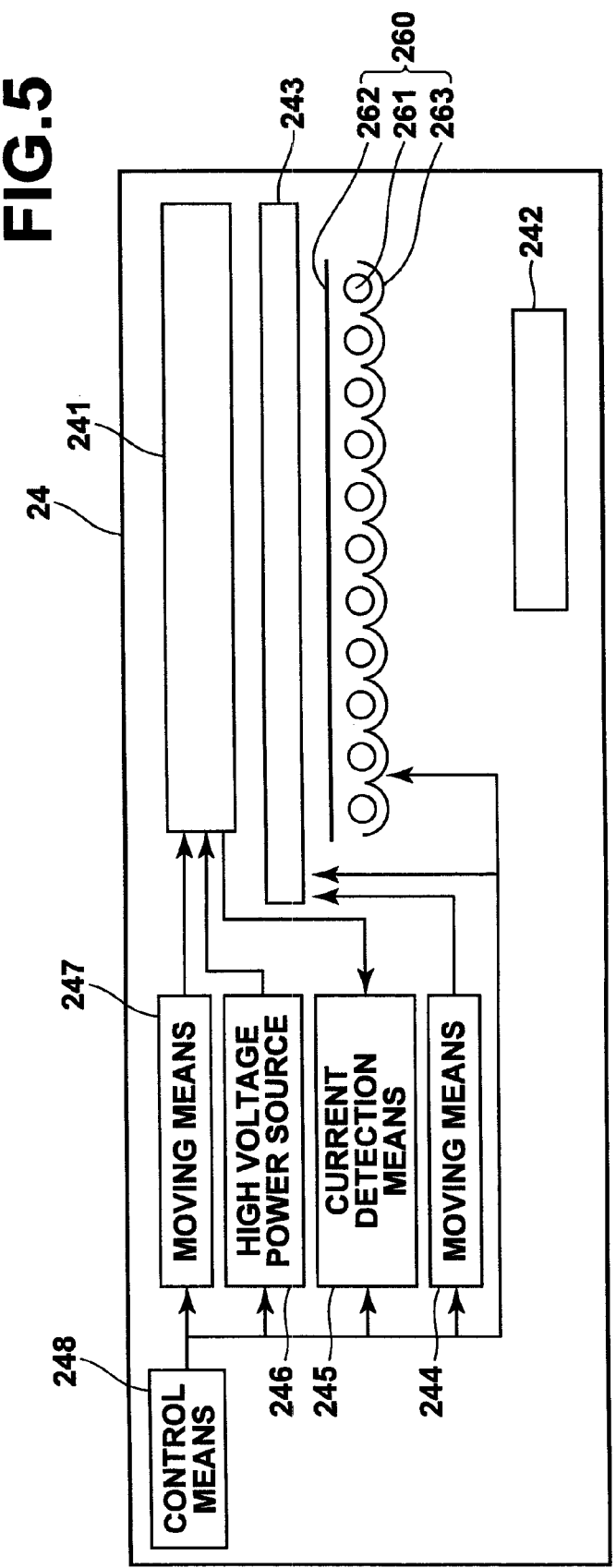
FIG. 5 schematically illustrates inside of the imaging platform of the breast image obtaining unit.

As for the pre-exposure light source section 260, a light source that illuminates/extinguishes in a short time with very little afterglow is required. In the present embodiment, therefore, an external electrode type rare gas fluorescent lamp is used. More specifically, as illustrated in FIG. 5, the pre-exposure light source section 260 includes: a plurality of external electrode type rare gas fluorescent lamps 261 extending in the direction perpendicular to the surface of the drawing; a wavelength selection filter 262 provided between the florescent lamps 261 and solid state detector 241; and a reflector 263 for reflecting light emitted from the fluorescent lamps 261 to the solid state detector 241 effectively. The pre-exposure light needs just to be irradiated on the entire surface of the second electrode layer 415 of the solid state detector 241, and a particular condenser means is not required, but a narrow luminance distribution is desirable. As for the light source, for example, LED chips disposed two dimensionally may be used instead of the fluorescent lamps.

The moving means 247 includes a linear motor or the like (not shown), and reciprocally translates the solid state detector 241 between the imaging position and readout position.

In the present embodiment, an optical readout type solid state detector is used as the flat panel detector as an example. Alternatively, a TFT readout type solid state detector may also be used as the flat panel detector as described, for example, in Japanese Unexamined Patent Publication Nos. 2004-080749, 2004-073256. In the TFT readout type solid state detector, the signal charges stored in the storage section of the solid state detection element are read out by scan driving the TFTs connected to the storage section.

The dose detector 242 is disposed under the solid state detector 241, and as the dose detector 242, for example, an AEC sensor in which semiconductor detectors are disposed as the sensor for measuring the dose of radiation may be used. Alternatively, the dose detector 242 may be adapted to detect the dose of radiation irradiated on the solid state detector 241 (or TFT type flat panel detector). Hereinafter, the description will be made of a case in which AEC sensor is used as the dose detector 242 in the present embodiment.

Figure 9:
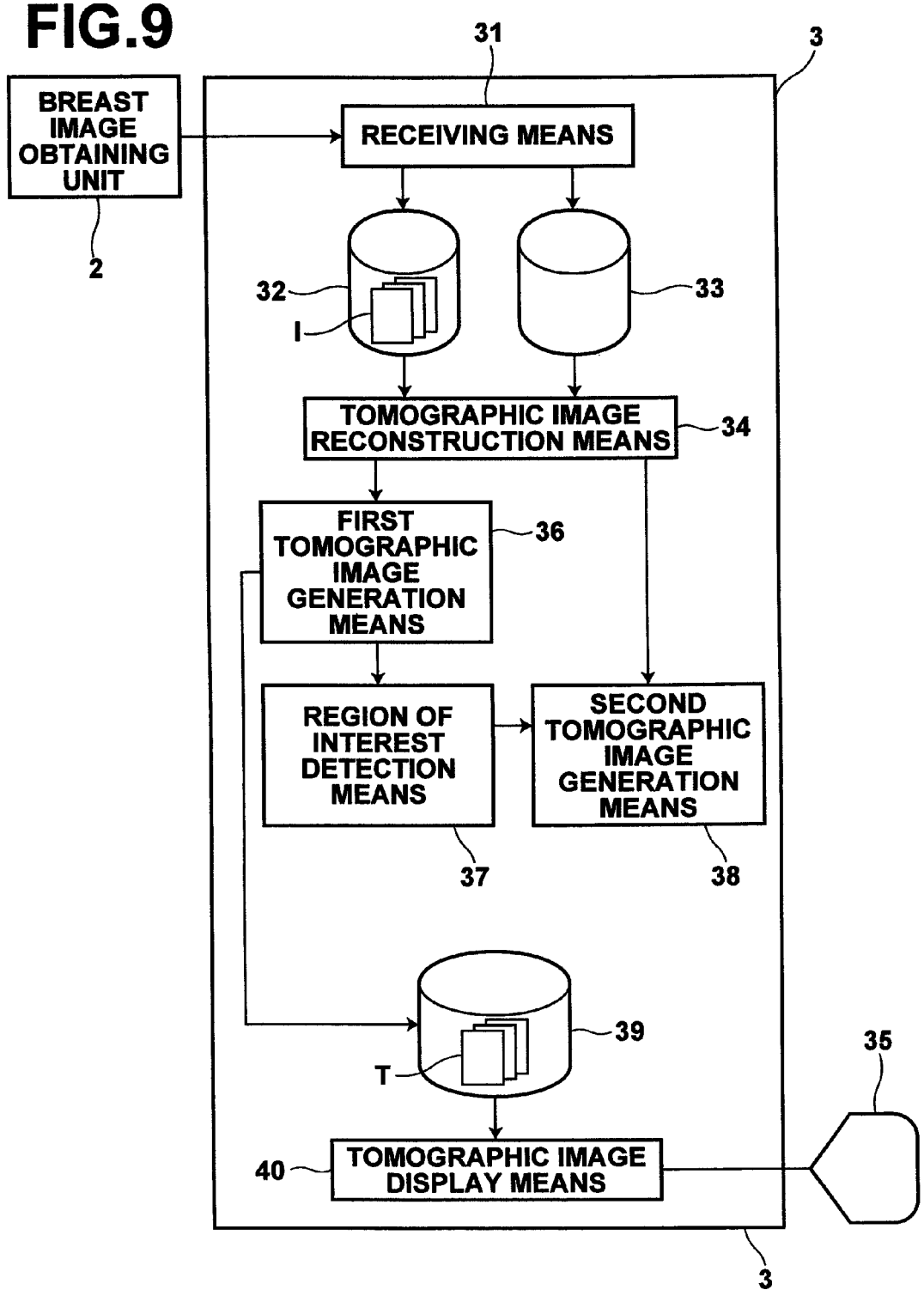
FIG. 9 is a block diagram of the tomographic image generation unit according to a first embodiment.

FIG. 9 is a schematic block diagram of the tomographic image generation unit 3 according to the present embodiment.

The tomographic image generation unit 3 includes: a receiving means 31 for receiving radiation images I obtained by the breast image obtaining unit 2 and data, such as the imaging conditions or the like; a radiation image storage means 32 for storing the radiation images I; an imaging condition storage means 33 for storing imaging conditions received from the breast image obtaining unit 2; a tomographic image reconstruction means 34 for reconstructing a tomographic image T from a plurality of radiation images I; and a first tomographic image generation means 36 for generating a plurality of tomographic images with a first slice interval using the tomographic image reconstruction means 34. The tomographic image generation unit 3 further includes: a region of interest detection means 37 for detecting a region of interest from the tomographic images T generated with the first slice interval; a second tomographic image generation means 38 for generating tomographic images with a smaller slice interval adjacent to the slice position of a tomographic image T in which the region of interest is detected using the tomographic image reconstruction means 34; a tomographic image storage means 39 for storing generated tomographic images T; a display section 35 for displaying the tomographic images T; and a tomographic image display means 40 for causing the tomographic images T to be displayed on the display section 35 in the order of the depth of the tomographic images T.

The radiation image storage means 32 is a large capacity storage device, such as a hard disk. The radiation image storage means 32 stores a plurality of radiation images I obtained by the breast image obtaining unit 2 by moving the radiation source 22 to each of the positions S1, S2, S3, - - - , Sn.

Figure 10:
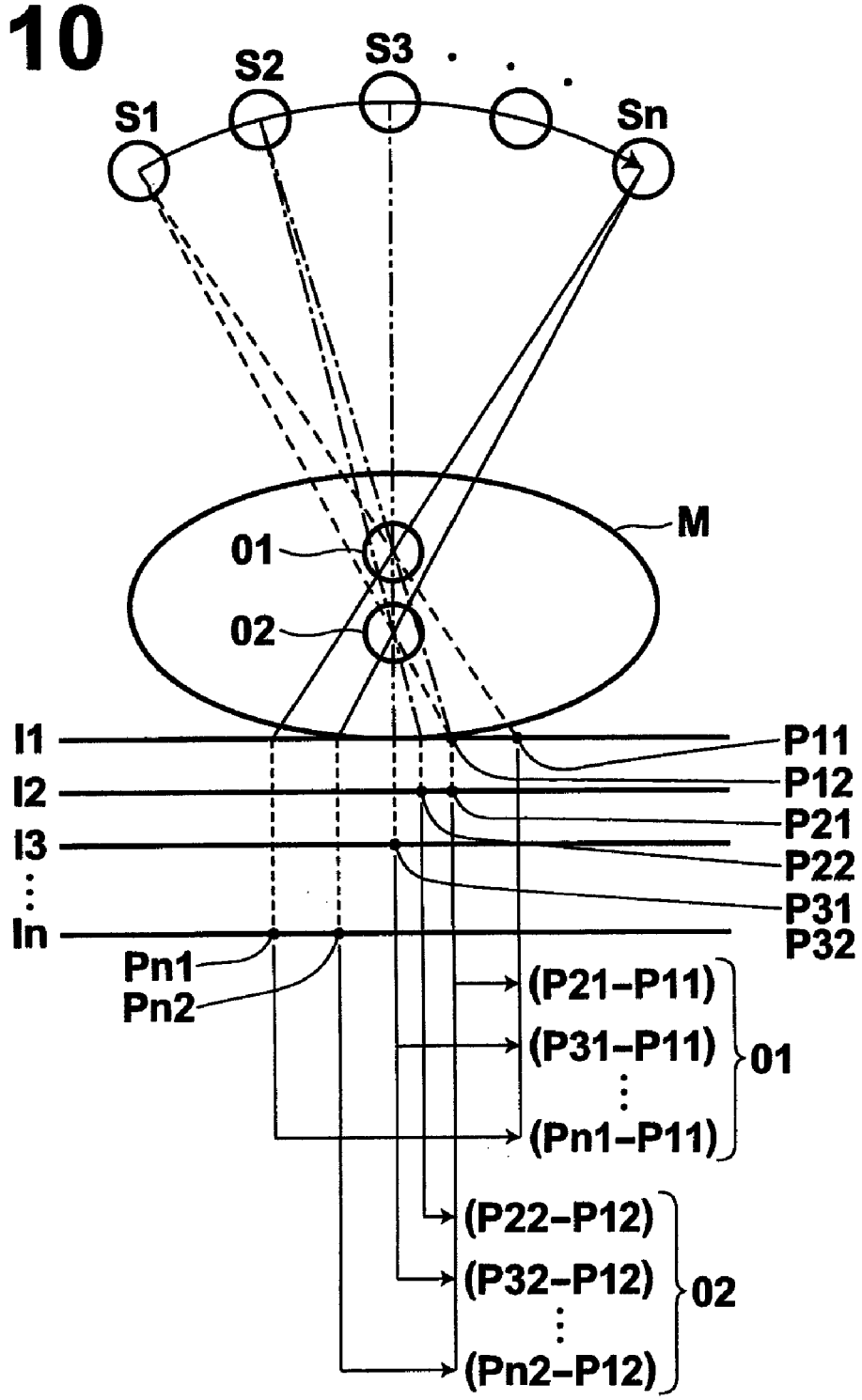
FIG. 10 illustrates a method for reconstructing a tomographic image from a radiation image.

The tomographic image reconstruction means 34 generates a tomographic image from the plurality of radiation images I obtained in the positions S1, S2, S3, - - - , Sn. As illustrated in FIG. 10, it is assumed here that radiation images I1, I2, I 3, - - - , In are obtained when the breast M is imaged at different imaging angles with the radiation source placed at each of the positions S1, S2, S3, - - - , Sn. For example, when two objects (01, 02) existing at different depths are projected from the radiation source position S1, they are projected on the radiation image I1 at positions P11 and P12 respectively. When the objects (01, 02) are projected from the radiation source position S2, they are projected on the radiation image I2 at positions P21 and P22 respectively. In this way, if the objects (01, 02) are projected from different positions S1, S2, S3, - - - , Sn while moving the radiation source 22, the object 01 is projected at positions P11, P21, P31, - - - , Pn1 in correspondence with each position of the radiation source 22, while the object 02 is projected at positions P12, P22, P32, - - - , Pn2.

If the cross-section where the object 01 exists is desired to be emphasized, the radiation image I2 is moved by the amount of (P21-P11), radiation image I3 is moved by the amount of (P31-P11), so on, and radiation image In is moved by the amount of (Pn1-P11), then added together. In this way, a tomographic image emphasizing the structure on the cross section located at the depth of the object 01 is generated. If the cross-section where the object 02 exists is desired to be emphasized, the radiation image I2 is moved by the amount of (P22-P12), radiation image I3 is moved by the amount of (P32-P12), so on, and radiation image In is moved by the amount of (Pn2-P12), then added together. In this way, by aligning each of the radiation images I1, I2, I3, - - - , In according to the slice position and added together, a tomographic image parallel to the detection surface of each depth is reconstructed.

The position on the radiation images I where an object existing at each depth is projected differs depending on the imaging angle, i.e., the position of the radiation source 22 irradiating the radiation. Thus, the tomographic image reconstruction means 34 calculates moving amounts for the radiation images I1, I2, I3, - - - , In based on the imaging angle included in the imaging conditions of the breast image obtaining unit 2 stored in the imaging condition storage means 33 and reconstructs a tomographic image.

The first tomographic image generation means 36 generates a tomographic image with a predetermined first slice interval using the tomographic image reconstruction means 34.

The region of interest detection means 37 analyzes the tomographic image created from the radiation images to detect a region of observation object, such as a tumor or the like, as a region of interest.

For example, a tumor pattern appearing on an image obtained using radiation generally has a rounded contour, and is observed as a region having a greater pixel value in comparison with the surrounding area. Such tumor pattern is a region having a hemispherical shape with densities extending concentrically (circular convex region). It has a density gradient in which the density value is highest in the periphery and gradually decreases toward the center. The density gradients converge toward the center, and are calculated as gradient vectors, and a pattern, such as a tumor pattern, may be detected based on the convergence index of the gradient vector ("Characteristics Analysis of Convergence Index Filters" by Jun Wei et al., Vol. J84-D-II, No. 7, pp. 1289-1298, 2001, The Institute of Electronics, Information and Communication Engineers, or "Convergence Index Filter for Detection of Lung Nodule Candidates" by Jun Wei et al., Vol. J83-D-II, No. 1, pp. 118-125, 2000, The Institute of Electronics, Information and Communication Engineers).

More specifically, the convergence index is obtained in the following manner. First, for all of the pixels of a target image to be calculated, orientations of gradient vectors of the image data is obtained based on Formula (1) below.

$$\varphi = \tan^{-1} \frac{(f_{11} + f_{12} + f_{13} + f_{14} + f_{15}) - (f_{51} + f_{52} + f_{53} + f_{54} + f_{55})}{(f_{15} + f_{25} + f_{35} + f_{45} + f_{55}) - (f_{11} + f_{21} + f_{31} + f_{41} + f_{51})} \quad (1)$$

where, f11 to f55 are pixel values (image data) of the pixels on the periphery of a mask of 5×5 pixels centered on the attention pixel j, as illustrated in FIG. 11.

Figure 13:
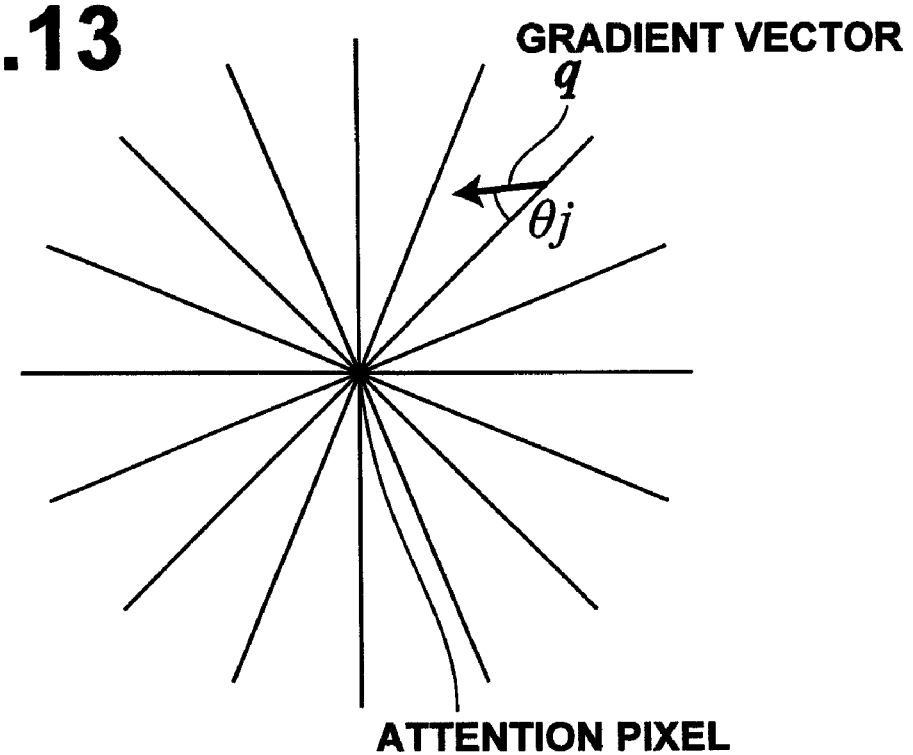
FIG. 13 illustrates the relationship between a gradient vector and an attention pixel (part 2).

Then, for each of the pixels of the target image, a convergence index C is calculated according to Formula (2) below.

$$C = (1/N) \sum_{j=1}^{N} \cos\theta_j \quad (2)$$

where, N is the number of pixels within a circle of a radius of 1 centered on the attention pixel; and θj is an angle formed between a straight line connecting the attention pixel and each pixel j within the circle, and the gradient vector at the pixel j obtained by Formula (1) above (FIGS. 12 and 13). Accordingly, the convergence index C becomes a great value for the pixel to which the orientation of the gradient vector of each pixel j is converged.

Figure 14:
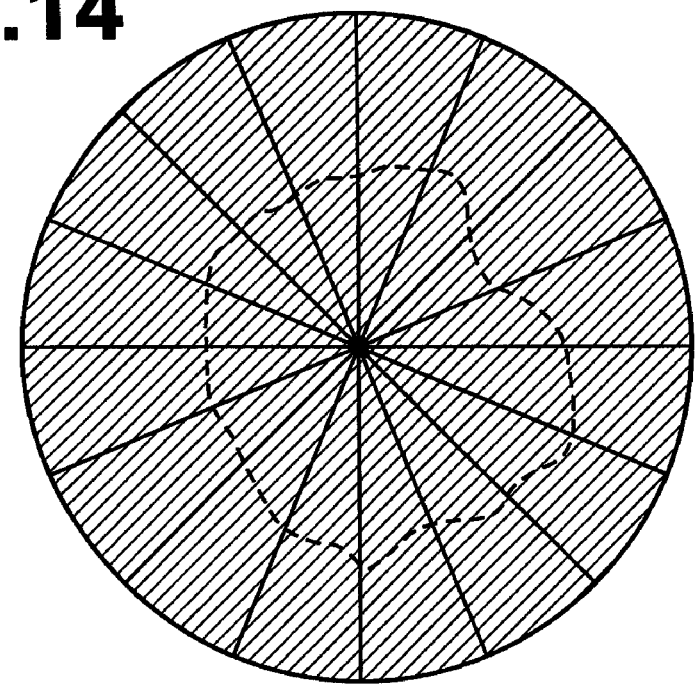
FIG. 14 illustrates a region of interest.

That is, the gradient vector of each pixel j adjacent to a tumor pattern is oriented to substantially the center of the tumor pattern, regardless of the magnitude of contrast of the tumor pattern, therefore the pixel having a large convergence index can be said to be the center pixel of the tumor pattern. On the other hand, in a line pattern, such as a blood vessel or the like, the orientations of the gradient vectors are biased to a certain direction, so that the value of the convergence index is relatively low. Accordingly, a region of interest, such as a tumor pattern (region enclosed by a dotted line in FIG. 14) may be detected by calculating the convergence index C of each pixel forming an image with respect to the attention pixel, and evaluating the convergence index C to see whether or not it exceeds a predetermined threshold value.

Some of such evaluation means for evaluating the convergence index have a devised filter in the size or shape thereof in order to provide a detection power not influenced by the size or shape of a tumor, and the iris filter is one of the typical filters of such type. The iris filter may extract a region where the output range of the filter becomes maximal as the region of interest.

The region of interest may also be detected in the following manner. That is, further obtaining density histograms within the region detected by the iris filter or the like; calculating a plurality of characteristic amounts including, for example, dispersion value, contrast, angular moment, and the like; defining each characteristic amount by a predetermined weighting function to obtain a new evaluation value; determining whether or not the region detected by the iris filter is a malignant pattern based on the obtained new evaluation values; and detecting only the malignant pattern as the region of interest (for more information, refer to, for example, Japanese Unexamined Patent Publication Nos. 8 (1996)-294479, and 9(1997)-167238 proposed by the applicant of the present invention).

The characteristic amounts described above may include dispersion value, bias, correlation value, moment, entropy of edge information representing the characteristics of the edge portion of the region detected by the iris filter.

Further, Mahalanobis distance may be used as an evaluation value. More specifically, Mahalanobis distance Dm1 to the pattern class indicating a benign pattern (i=1), and Mahalanobis distance Dm2 to the pattern class indicating a malignant pattern (i=2) are calculated. If the Mahalanobis distance Dm1 to the pattern class indicating a benign pattern is smaller than the Mahalanobis distance Dm2 to the pattern class indicating a malignant pattern, i.e., Dm1<Dm2, it is determined to be a benign pattern, and if the Mahalanobis distance Dm2 to the pattern class indicating a malignant pattern is smaller than the Mahalanobis distance Dm1 to the pattern class indicating a benign pattern, i.e., Dm1>Dm2, it is determined to be a malignant pattern, and only the region determined to be malignant is detected as the region of interest (for more information, refer to, for example, Japanese Unexamined Patent Publication No. 2002-074325 proposed by the applicant of the present invention).

The second tomographic image generation means 38 generates tomographic images with a second slice interval which is smaller that the first slice interval adjacent to the slice position of the tomographic image from which a region of interest is detected. If a region of interest seeming like a tumor is detected from a tomographic image generated with the first slice interval, the observer desires to observe the region by slicing the image with a smaller slice interval adjacent to the region. Consequently, tomographic images are additionally generated with a smaller slice interval before and after the slice position where the region of interest is detected using the tomographic image reconstruction means 34.

The tomographic image display means 40 causes tomographic images to be sequentially switched and displayed on the display section 35 in the order of the depth of the tomographic images. Here, the observer may intuitively know the size of a tumor or the like appearing in the region of interest by making the switching speed of the tomographic images constant with respect to the change in the depth. Consequently, the time interval for displaying the tomographic images generated with the second slice interval is made shorter than that for displaying the tomographic images generated with the first slice interval to cause the change in the depth of the displayed tomographic images to become temporally constant.

Preferably, a high definition display device appropriate for diagnosis is used in the display section 35.

A specific flow from obtaining radiation images of a breast M of a subject to generating a tomographic images using the radiation tomographic image obtaining apparatus 1 according to the present embodiment will now be described.

Figure 15:
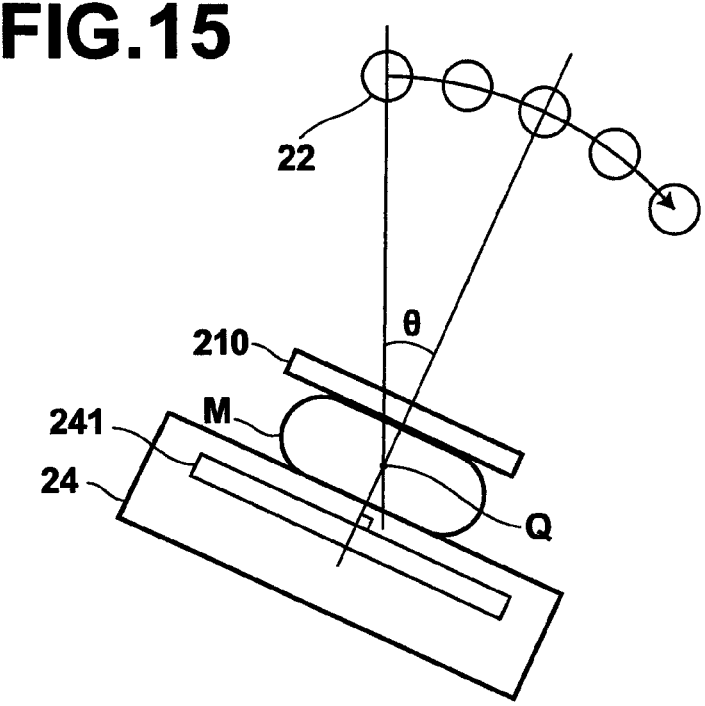
FIG. 15 illustrates the relationship between the inclination of the pressing plate and the position of a breast.

When the subject stands on the side of the breast image obtaining unit 2 for imaging the breast M, the operator inputs the height of the arm according to the height of the subject, and the rotation angle of the arm according to the size and shape of the breast M from the operation section, such as an operation panel, and the height and rotational angle of the arm 25 are adjusted by the arm moving means 29 according to the inputted height and rotational angle. In MLO imaging, the imaging platform 24 is inclined at an angle in the range from 45 to 80° from the horizontal direction of the imaging platform 24 so that the imaging platform 24 becomes parallel to the chest muscles of the subject (FIG. 15). Generally, the imaging platform 24 is inclined around 60° from the horizontal direction for imaging. In CC imaging, the imaging platform 24 is maintained in the horizontal direction and the height is adjusted.

The breast M is placed on the imaging surface of the imaging platform 24 such that the radiation irradiated from the radiation source 22 passes through the center of the breast M when the imaging angle θ=0. That is, the breast M is placed such that the radiation source 22 is positioned on the normal line extending from the detection surface of the radiation image detector 241 and passing through the center of the breast M, as illustrated in FIG. 15.

The breast M is a solid organ having a certain thickness, so that if the breast M is imaged directly, a tumor may not be imaged due to interference by the mammary glands, fat, blood vessels, and the like. Therefore, in the mammography screening, the breast M is clamped by the pressing plate 210 to stretch it thinly so that the shadow of any small lump is clearly imaged with a small amount of radiation. Thus, the breast M is compressed with the pressing plate 210 after the imaging platform 24 is adjusted to an appropriate height and an inclination.

Checking the pressurized state of the breast M, the operator inputs an instruction to gradually increase the pressure on the breast M through the operation panel, foot switch, or the like. Then, according to the inputted instruction, the pressing plate moving means 252 gradually presses down the pressing plate 210 in the longitudinal direction of the arm 25. For example, the pressing pressure is increased by 1 kg every time the foot switch is depressed, and the foot switch is depressed continuously until the thickness of the breast M becomes appropriate for imaging. Alternatively, a configuration may be adopted in which the pressing plate 210 gradually increases the pressure after it is moved downward and touched on the breast M.

After the pressing process is completed, imaging of the breast M is initiated, and radiation images I1, I2, - - -, In are obtained by moving the radiation source 22 of the radiation accommodation section 23 to each of the positions S1, S 2, - - -, Sn and irradiating radiation from the radiation source 22.

The tomographic image generation unit 3 receives a plurality of radiation images I1, I2, - - -, In obtained by the breast image obtaining unit 2 and the imaging conditions through the receiving means 31, and stores the radiation images I1, I2, - - -, In and the imaging conditions in the radiation image storage means 32 and imaging condition storage means 33 respectively.

Figure 16:
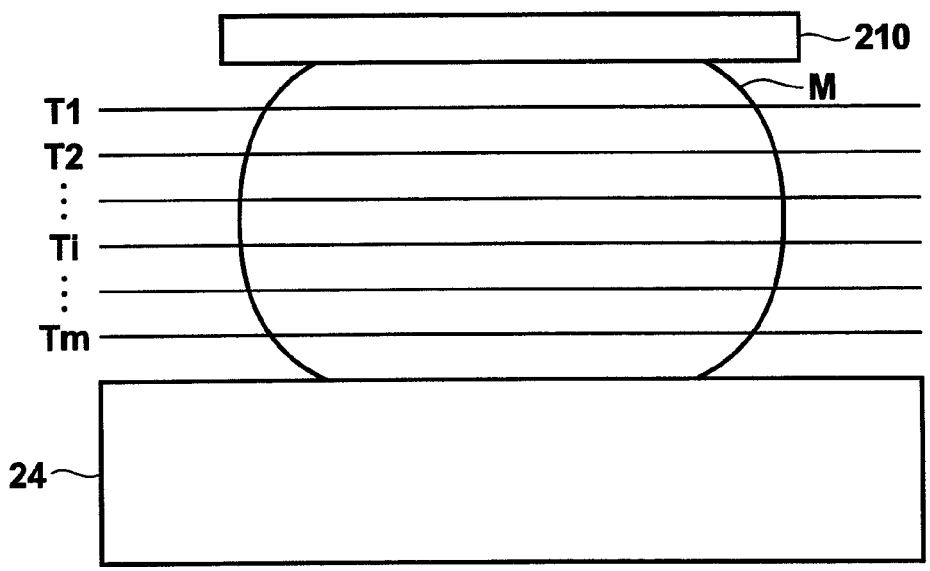
FIG. 16 illustrates the relationship between the imaging platform and cross-section.

The first tomographic image generation means 36 reconstructs a tomographic image from the radiation images I1, I2, - - -, In at each slice position sliced with a first slice interval d1 using the tomographic image reconstruction means 34 according to the imaging conditions stored in the imaging condition storage means 33 to generate tomographic images T1, T2, - - -, Ti, - - -, Tm as illustrated in FIG. 16 and stores in the tomographic image storage means 39.

Detection of a region of interest is performed on each of the generated tomographic images T1, T2, - - -, Tn by the region of interest detection means 37. If a region of interest is detected from a tomographic image Ti, additional tomographic images are generated at each slice position sliced with a second slice interval, which is smaller than the first slice interval, by the second tomographic image generation means 38 within the range from a tomographic image Ti−1 immediately preceding the tomographic image Ti to a tomographic image Ti+1 immediately following the tomographic image Ti as illustrated in FIG. 17.

If a region of interest is detected from each of the tomographic images Ti and Ti+1 at substantially the same position, it is likely that a tumor or the like is extending between the tomographic images Ti and Ti+1. Therefore, tomographic images with the smaller second slice interval are additionally generated and stored in the tomographic image storage means 39.

The tomographic image display means 40 causes the display section 35 to display the tomographic images T1, T2, - - -, Tm stored in the tomographic image storage means 39 in the order of the depth. Further, when the tomographic images T1, T2, - - -, Tm are displayed, they are displayed such that the switching speed of the tomographic images becomes constant with respect to the change in the depth.

Figure 17:
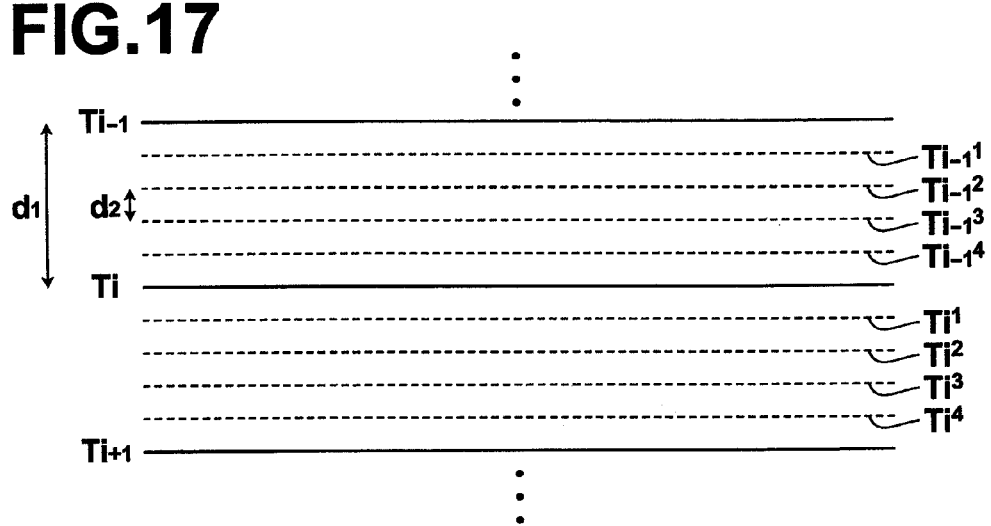
FIG. 17 illustrates the relationship between a first slice interval and a second slice interval.

Assuming a case, for example, in which a region of interest is detected on the tomographic image Ti, and tomographic images Ti−$1^1$, Ti−$1^2$, Ti−$1^3$, and Ti−$1^4$ are added between the tomographic images Ti−1 and Ti, and tomographic images Ti$^1$, Ti$^2$, Ti$^3$, and Ti$^4$ between the tomographic images Ti and Ti+1 with a smaller second slice interval d2=d1/5, as illustrated in FIG. 17. Here, if the tomographic images T1, T2, - - -, Ti−1 and Ti+1- - -, Tm are displayed at an interval of 1 ms, the tomographic images Ti−1, Ti−$1^1$, Ti−$1^2$, Ti−$1^3$, Ti−$1^4$, Ti, Ti$^1$, Ti$^2$, Ti$^3$, Ti$^4$ are displayed at an interval of 200 ms.

As described above in detail, the slice interval is made smaller in the area adjacent to the slice position where a region of interest is found, and the change in the depth of the displaying tomographic images is made constant. This allows the observer to correctly recognize the shape of a tumor or the like imaged in the region of interest and to know the size and position thereof accurately.

In the embodiment above, description has been made of a case in which the radiation accommodation section 23 is rotated around the spindle C to move the radiation source 22 in arc. Alternatively, the radiation source 22 may be moved in arc within a locked radiation accommodation section 23.

In the first embodiment described above, the time interval for displaying tomographic images generated with the second slice interval is made shorter than that for displaying tomographic images generated with the first slice interval so that the change in the depth of displayed images becomes temporally constant. The display method is not limited to this, and the display interval may be made constant regardless of slice interval, or display time may be set longer for the region of the smaller slice interval. This allows the region of interest to be observed more carefully.

Next, a second embodiment of the present invention will be described. In the present embodiment, description will be made of a case in which two sets of tomographic images generated respectively from two sets of radiation images of the same region of the same subject are displayed side by side.

The radiation tomographic image obtaining apparatus 1 according to the present embodiment has the same configuration as that of the first embodiment. Therefore, it will not be elaborated upon further here, and only a flow from generating two sets of tomographic images from two sets of radiation images to displaying them side by side will be described.

As in the first embodiment, the imaging platform 24 of the breast image obtaining unit 2 is adjusted to an appropriate height and an inclination for imaging and tomosynthesis imaging is performed while pressing a breast M with the pressing plate 210. Two sets of radiation images obtained in the manner as described above are stored in the radiation image storage means 32. The two sets of radiation images are images of the same breast M obtained at different times. The set of radiation images obtained at older time are designated as past images, and the set of radiation images obtained recently are designated as current images.

First, the first tomographic image generation means 36 reconstructs a tomographic image from the past radiation images I1-old, I2-old, - - -, In-old at each slice position sliced with the first slice interval d1 using the tomographic image reconstruction means 34 according to the imaging conditions of the past images stored in the imaging condition storage means 33 to generate tomographic images T1-old, T2-old, - - - Tm-old and stores in the tomographic image storage means 39. Likewise, it reconstructs a tomographic image from the current radiation images I1-new, I2-new, - - -, In-new at each slice position sliced with the first slice interval d1 using the tomographic image reconstruction means 34 according to the imaging conditions of the current images stored in the imaging condition storage means 33 to generate tomographic images T1-new, T2-new, - - - Tm-new and stores in the tomographic image storage means 39.

Detection of a region of interest is performed on each of the generated tomographic images T1-old, T2-old, - - -, Tn-old and T1-new, T2-new, - - -, Tm-new by the region of interest detection means 37. If a region of interest is detected, tomographic images with the smaller second slice interval d2 are additionally generated by the second tomographic image generation means 38.

Figure 18:
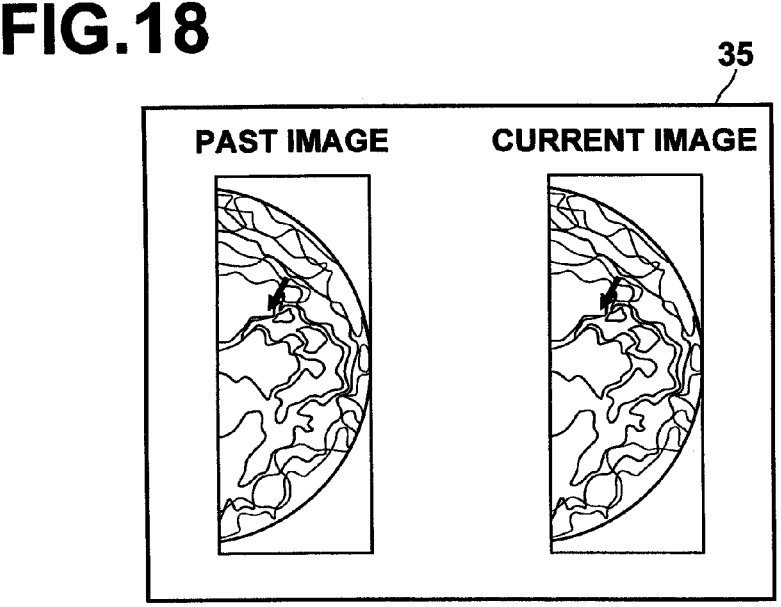
FIG. 18 illustrates an example case where tomographic images are displayed side by side.
Figure 19:
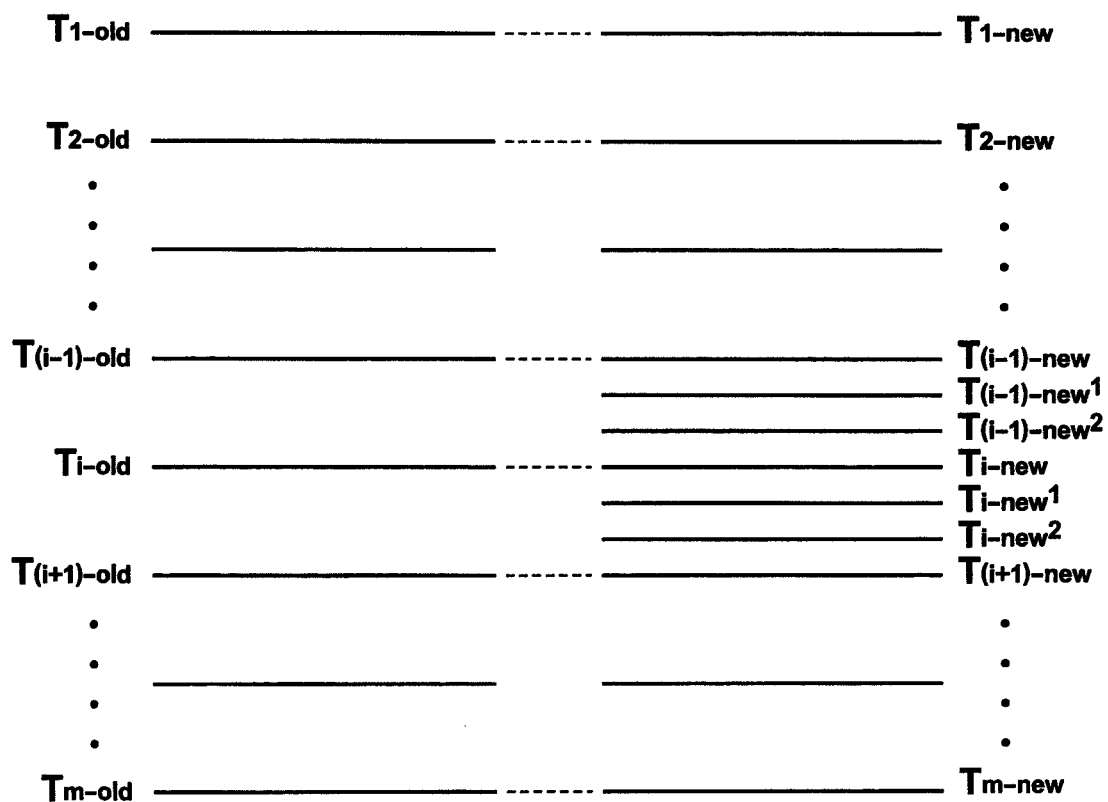
FIG. 19 illustrates correspondence between tomographic images of past and current images.

The tomographic image display means 40 causes the display section 35 to display the two sets of tomographic images T1-old, T2-old, - - -, Tm-old (past images), and tomographic images T1-new, T2-new, - - -, Tm-new (current images) stored in the tomographic image storage means 39 side by side in the order of the depth, as illustrated in FIG. 18. When the tomographic images T1, T2, - - -, Tm are displayed, they are displayed such that the switching speed of the tomographic images becomes constant with respect to the change in the depth. Further, when the two sets of tomographic images T1-old, T2-old, - - -, Tm-old (past images), and tomographic images T1-new, T2-new, - - -, Tm-new (current images) are displayed side by side in the order of the depth, tomographic images of the same depth, each in each of the sets of tomographic images are displayed at the same time. For example, as illustrated in FIG. 19, if tomographic images T(i−1)-new$^1$, T (i−1)-new$^2$, and Ti-new$^1$, Ti-new$^2$ are additionally generated with a smaller slice interval before and after Ti-new respectively, T(i−1)-new$^1$, T(i−1)-new$^2$ are displayed while T(i−1)-old and Ti-old are displayed, and Ti-new$^1$, Ti-new$^2$ are displayed while Ti-old and T(i+1)-old are displayed.

In the present embodiment, the past and current images have been described, but radiation images of symmetrical organs, such as right and left breasts, may be reconstructed.

As illustrated in FIG. 22, when displaying the right and left breasts, an indicator (dotted line) may be displayed on the image indicating the thickness of the breasts (area a in FIG. 22) to indicate the slice position of the tomographic image of the breasts. FIG. 22 illustrates an example in which right and left breasts imaged in MLO direction are displayed side by side. Similar display is possible when the past and current images are displayed. The display of such indicator is not limited to the case where images for comparison are displayed side by side, but also in the case where only the tomographic images of the right or left breast are displayed. The display of the indicator enables the observer to know the position being observed.

As described above, in the second embodiment, past and current images are displayed side by side, and images are switched such that the tomographic images of the same depth in the past and current image sets are displayed at the same time. This allows the difference between the past and present to be easily recognized.

Next, a third embodiment of the present invention will be described in detail with reference to the accompanying drawings. In the present embodiment, description will be made of a case in which the region of interest detection means performs detection for a region of interest on each tomographic image with reference to a region of interest detected from a radiation image obtained through high dose imaging.

Figure 20:
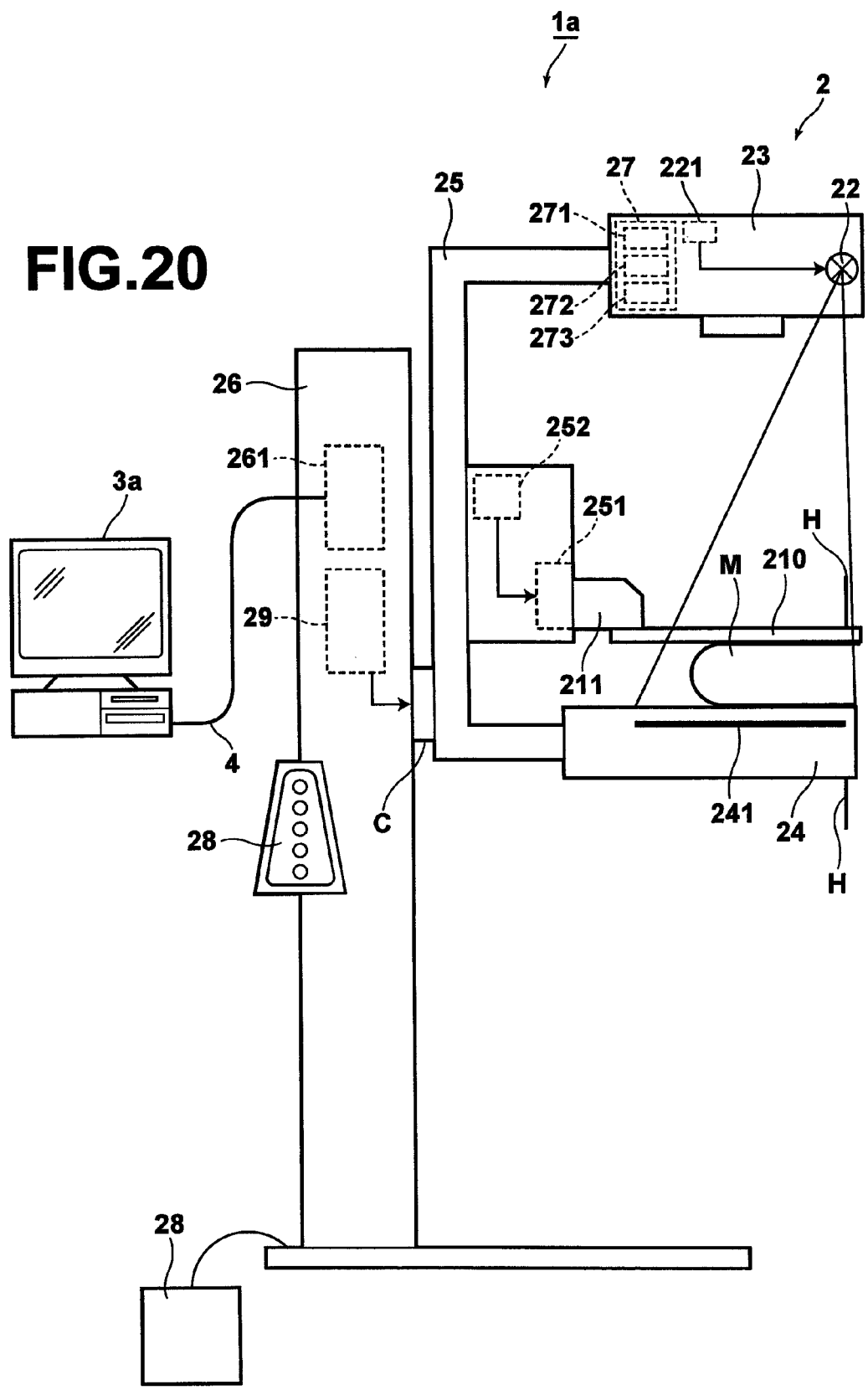
FIG. 20 is a block diagram of the radiation tomographic image obtaining apparatus according to a third embodiment of the present invention.
Figure 21:
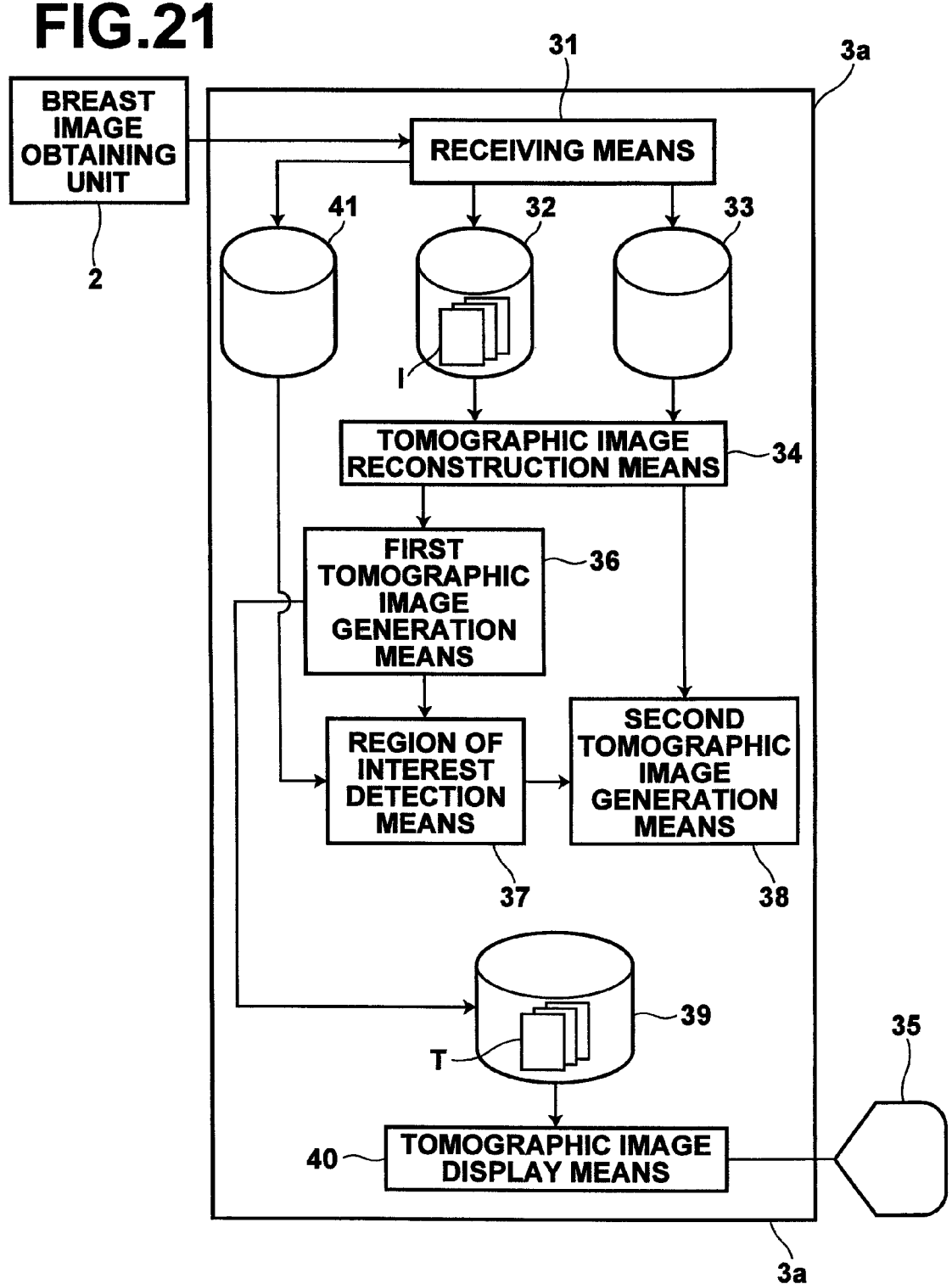
FIG. 21 is a block diagram of the tomographic image generation unit according to a third embodiment.

The configuration of the radiation tomographic image obtaining apparatus 1a according to the present embodiment is illustrated in FIGS. 20 and 21. Components identical to those in the previous embodiments will be given the same reference numerals and will not be elaborated upon further. Here, description will be made only for those different from the previous embodiments.

The radiation tomographic image obtaining apparatus 1a includes: the breast image obtaining unit 2 for obtaining a plurality of radiation images of a breast M of a subject by irradiating radiation to the breast M from different directions; a tomographic image generation unit 3a for generating a tomographic image by reconstructing the plurality of radiation images obtained by the breast image obtaining unit 2; and the network 4 linking the breast image obtaining unit 2 and the tomographic image generation unit 3a.

The tomographic image generation unit 3a includes: the receiving means 31 for receiving radiation images I obtained by the breast image obtaining unit 2 and data, such as the imaging conditions or the like; the radiation image storage means 32 for storing the radiation images I; the imaging condition storage means 33 for storing imaging conditions received from the breast image obtaining unit 2; the tomographic image reconstruction means 34 for reconstructing a tomographic image T from a plurality of radiation images I; and the first tomographic image generation means 36 for generating a plurality of tomographic images with a first slice interval using the tomographic image reconstruction means 34. The tomographic image generation unit 3a further includes: the region of interest detection means 37 for detecting a region of interest from the tomographic images T generated with the first slice interval; the second tomographic image generation means 38 for generating tomographic images with a smaller slice interval adjacent to the slice position of a tomographic image T in which the region of interest is detected using the tomographic image reconstruction means 34; the tomographic image storage means 39 for storing generated tomographic images T; the display section 35 for displaying the tomographic images T; the tomographic image display means 40 for causing the tomographic images T to be displayed on the display section 35 in the order of the depth of the tomographic images T; and a high dose image storage means 41.

Each of the plurality of radiation images used for the reconstruction is obtained by irradiating low dose radiation in order to reduce the radiation dose received by the subject. The high dose image is an image obtained by irradiating higher dose radiation to the subject than the radiation for imaging each of the plurality of radiation images used for the reconstruction of tomographic image, that is, a radiation image obtained by plain X-ray imaging in which the imaging is performed only once.

The high dose image includes mammary glands, fat, and the like of the breast M overlapped with each other, but it is a clear image.

First, the region of interest detection means 37a performs detection on the high dose image for a region of interest, and with reference to the position of a detected region of interest, detects a region of interest located adjacent to the position from other plurality of tomographic images. When a tumor is extending between a plurality of tomographic images, this facilitates the determination as to whether or not the region of interest in each of the tomographic images is a pattern of the same tumor.

A specific flow from obtaining radiation images of a breast of a subject to generating tomographic images using the radiation tomographic image obtaining apparatus 1a according to the present embodiment will now be described.

As in the previous embodiment, the imaging platform 24 of the breast image obtaining unit 2 is adjusted to an appropriate height and an inclination for imaging and the breast M is pressed with the pressing plate 210.

After the pressing process is completed, a high dose image is obtained by irradiating radiation on the breast M with the same radiation dose as that for obtaining a mammogram through plain X-ray imaging.

Further, tomosynthesis imaging of the breast M is initiated, and radiation images I1, I2, - - - , In are obtained by moving the radiation source 22 of the radiation accommodation section 23 to each of the positions S1, S2, - - - , Sn and irradiating radiation from the radiation source 22.

The high dose image and radiation images I1, I2, - - - , In obtained by the breast image obtaining unit 2 are sent to the tomographic image generation unit 3a through the network. The high dose image is stored in the high dose image storage means 41, and radiation images I1, I2, - - - , In are stored in the radiation image storage means 32.

The method for generating tomographic images from the radiation images stored in the radiation image storage means 32 is identical to that of the first embodiment. Therefore, it will not be elaborated upon further here.

The region of interest detection means 37a performs detection on the high dose image for a region of interest, and with reference to the position of a detected region of interest, detects a region of interest located adjacent to the position from a plurality of tomographic images.

The display method for displaying the generated tomographic images is identical to that of the first or second embodiment. Therefore, it will not be elaborated upon further here.

Here, description has been made of a case in which high dose imaging is performed for a compressed breast, and immediately afterwards tomosynthesis imaging is performed. Alternatively, a mammogram obtained in the past with ordinary radiation dose may be used.

As described in detail, in the present embodiment, a region of interest is detected from tomographic images with reference to the position of a region of interest detected from a high dose image. This makes it easy to understand the relationship of region of interest between the tomographic images. Where additional tomographic images are generated with smaller slice interval, the slice interval may be appropriately adjusted using this information, thereby image display facilitating diagnosis may be achieved.

In the embodiments above, description has been made of a case in which a breast is imaged, but the present invention is also applicable to other regions such as chest, abdomen, and the like.

What is claimed is:

1. A radiation tomographic image generation apparatus, comprising:
   a radiation image storage means for storing a plurality of radiation images obtained from a radiation image detector by irradiating radiation to a subject on the radiation image detector from different directions by moving an irradiation section, which is provided opposite to the radiation image detector, to a plurality of positions and irradiating the radiation from the irradiation section in each of the positions;
   a tomographic image reconstruction means for reconstructing the plurality of images stored in the radiation image storage means to generate a tomographic image of the subject which is parallel to the detection surface of the radiation image detector;
   a first tomographic image generation means for generating a plurality of tomographic images with a first slice interval using the tomographic image reconstruction means;
   a region of interest detection means for detecting a region of interest from the tomographic images generated with the first slice interval, wherein said region of interest includes an abnormal tissue region; and
   a second tomographic image generation means for generating tomographic images with a second slice interval, which is smaller than the first slice interval, adjacent to a slice position of a tomographic image from which a region of interest, including the abnormal tissue region, is detected by the region of interest detection means using the tomographic image reconstruction means.

2. The radiation tomographic image generation apparatus of claim 1, wherein:
   the apparatus further comprises a high dose image storage means for storing a high dose image obtained by irradiating higher dose radiation to the subject than the radiation for obtaining the plurality of radiation images used for the reconstruction of tomographic image; and
   the region of interest detection means is a means for detecting a region of interest from the high dose image and, in consideration of the position of the detected region of interest, detecting a region of interest from each of the tomographic images.

3. The radiation tomographic image generation apparatus of claim 1, wherein:
   the apparatus further comprises a tomographic image display means for sequentially displaying the tomographic images in the order of the depth thereof; and
   the tomographic image display means is a means for performing the display such that the change in the depth of displaying tomographic images becomes temporally constant by making the time interval for displaying the tomographic images generated with the second slice interval shorter than the time interval for displaying the tomographic images generated with the first slice interval.

4. The radiation tomographic image generation apparatus of claim 3, wherein the tomographic image display means is a means for displaying two sets of tomographic images, generated respectively from two sets of radiation images of the same region or symmetrical regions of the subject, side by side on the screen by switching the tomographic images in the order of the depth thereof, and such that the tomographic images of the same depth, each in each of the sets of tomographic images, are displayed at the same time.

5. The apparatus of claim 1, wherein said region of interest is a partial section of the first slice.

6. A non-transitory computer-readable recording medium, on which a program for causing a computer to perform the following functions is recorded:
   a tomographic image reconstruction means for reconstructing a plurality of radiation images stored in a radiation image storage means storing a plurality of radiation images obtained from a radiation image detector by irradiating radiation to a subject on the radiation image detector from different directions by moving an irradiation section, which is provided opposite to the radiation image detector, to a plurality of positions and irradiating the radiation from the irradiation section in each of the positions to generate a tomographic image of the subject which is parallel to the detection surface of the radiation image detector;
   a first tomographic image generation means for generating a plurality of tomographic images with a first slice interval using the tomographic image reconstruction means;
   a region of interest detection means for detecting a region of interest from the tomographic images generated with the first slice interval, wherein said region of interest comprises an abnormal tissue region; and
   a second tomographic image generation means for generating tomographic images with a second slice interval, which is smaller than the first slice interval, adjacent to a slice position of a tomographic image from which a region of interest including the abnormal tissue region is detected by the region of interest detection means using the tomographic image reconstruction means.

7. The method of claim 6, wherein said region of interest is a partial section of the first slice.

* * * * *